(12) United States Patent
Yang

(10) Patent No.: US 10,750,267 B2
(45) Date of Patent: Aug. 18, 2020

(54) EARPLUG APPARATUS AND ELECTRONIC APPARATUS

(71) Applicant: SHENZHEN GOODIX TECHNOLOGY CO., LTD., Shenzhen (CN)

(72) Inventor: Wangwang Yang, Shenzhen (CN)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 16/168,785

(22) Filed: Oct. 23, 2018

(65) Prior Publication Data

US 2019/0174215 A1 Jun. 6, 2019

Related U.S. Application Data

(63) Continuation of application No. PCT/CN2017/114560, filed on Dec. 5, 2017.

(51) Int. Cl.
*H04R 25/00* (2006.01)
*H04R 1/10* (2006.01)
*H04R 3/00* (2006.01)
*G06F 3/01* (2006.01)
*A61B 5/00* (2006.01)

(52) U.S. Cl.
CPC ......... *H04R 1/1016* (2013.01); *A61B 5/6817* (2013.01); *G06F 3/011* (2013.01); *H04R 1/1091* (2013.01); *H04R 3/00* (2013.01)

(58) Field of Classification Search
CPC .... H04R 25/60; H04R 25/609; H04R 1/1016; A61B 5/1455
See application file for complete search history.

(56) References Cited

U.S. PATENT DOCUMENTS 5,949,896 A * 9/1999 Nageno ............... H04R 1/1016
381/328
6,556,852 B1 * 4/2003 Schulze ................... A61B 5/01
600/310

(Continued)

FOREIGN PATENT DOCUMENTS

CN 203951613 U 11/2014
CN 105100994 A 11/2015
(Continued)

*Primary Examiner* — Fan S Tsang
*Assistant Examiner* — Ryan Robinson

(57) ABSTRACT

An earplug apparatus and an electronic apparatus are provided. The earplug apparatus includes: a biological feature detection module, the biological feature detection module being arranged in the earplug apparatus and being configured to be fit in a region enclosed by an outer ear canal and an ear canal entrance; wherein the biological feature detection module comprises a light emitting unit and a light receiving unit, wherein the light emitting unit is configured to emit light to the enclosed region, the light emitted by the light emitting unit is processed by an ear tissue in the enclosed region and transmitted to the light receiving unit, and the light receiving unit is configured to convert the received light photoelectrically to generate an original electrical signal for biological feature detection. In this way, the entire size of the final product is small, and wearing comfort is enhanced.

15 Claims, 5 Drawing Sheets

(56) References Cited

U.S. PATENT DOCUMENTS

| | | | |
|---|---|---|---|
| 8,406,884 B2* | 3/2013 | Nielsen | A61B 5/0215 607/136 |
| 8,888,701 B2* | 11/2014 | LeBoeuf | G16Z 99/00 600/301 |
| 9,717,446 B2* | 8/2017 | Dixon | A61B 5/14551 |
| 9,955,919 B2* | 5/2018 | LeBoeuf | A61B 5/0077 |
| 10,015,582 B2* | 7/2018 | Wagner | A61B 5/6898 |
| 10,382,839 B2* | 8/2019 | Aumer | H04R 1/1091 |
| 2005/0177034 A1* | 8/2005 | Beaumont | A61B 5/14552 600/323 |
| 2005/0209516 A1* | 9/2005 | Fraden | A61B 5/02055 600/323 |
| 2008/0205679 A1* | 8/2008 | Darbut | H04R 25/554 381/328 |
| 2010/0192952 A1* | 8/2010 | Melker | A61M 16/0627 128/204.23 |
| 2012/0197093 A1 | 8/2012 | LeBoeuf et al. | |
| 2014/0187885 A1* | 7/2014 | Kreuzer | A61B 5/02055 600/324 |
| 2014/0213864 A1* | 7/2014 | Abdul-Hafiz | A61B 5/14552 600/325 |
| 2015/0351688 A1* | 12/2015 | Just | A61B 5/681 600/407 |
| 2017/0112671 A1* | 4/2017 | Goldstein | A61B 5/6817 |
| 2017/0258329 A1* | 9/2017 | Marsh | G01J 5/0215 |
| 2018/0020979 A1* | 1/2018 | Wagner | A61B 5/14552 600/379 |
| 2018/0055447 A1* | 3/2018 | Boesen | A61B 5/0002 |
| 2018/0096120 A1* | 4/2018 | Boesen | G06F 21/32 |
| 2018/0228381 A1* | 8/2018 | LeBoeuf | A61B 5/0059 |
| 2018/0353134 A1* | 12/2018 | Walter | A61B 5/14551 |
| 2019/0021670 A1* | 1/2019 | Yang | A61B 5/6816 |
| 2019/0029544 A1* | 1/2019 | Yang | A61B 5/02427 |
| 2019/0212198 A1* | 7/2019 | Marsh | A61B 5/01 |
| 2019/0253793 A1* | 8/2019 | Pedersen | H04R 1/40 |
| 2019/0282119 A1* | 9/2019 | Andersen | A61B 5/04004 |

FOREIGN PATENT DOCUMENTS

| | | |
|---|---|---|
| CN | 105379306 A | 3/2016 |
| CN | 204392514 U | 6/2016 |
| CN | 107041169 A | 8/2017 |
| EP | 2077091 A2 | 7/2009 |
| EP | 3128761 A1 | 2/2017 |
| JP | 5185265 B2 | 4/2013 |

* cited by examiner

EARPLUG APPARATUS AND ELECTRONIC APPARATUS

CROSS-REFERENCE TO RELATED APPLICATIONS

The present application is a continuation of international application No. PCT/CN2017/114560 filed on Dec. 5, 2017, which is hereby incorporated by reference in its entireties.

TECHNICAL FIELD

Embodiments of the present application relate to the technical field of biological feature detection, and in particular, relate to an earplug apparatus and an electronic apparatus.

BACKGROUND

Rapid development of smart devices, for example, emergence of smart earphones, facilitates practice of applications having a healthcare function, for example, detection of heart rate, blood oxygen and the like biological features. Specifically, these smart devices are used in scenarios of monitoring the heart rate and blood oxygen during exercise or movement to judge whether the biological feature of a user is normal, or monitoring the heart rate and blood oxygen during sleeping to judge whether the biological feature of a user is normal.

With regard to the practice of the above applications having the healthcare function, the current commonly used manner is: measuring the biological feature based on optical theories, for example, the light reflection law and the light transmission law. Using the light reflection law as an example, the light emitted by a light emitter is incident to the biological tissue and then reflected by the biological tissue, and a light receiver receives the reflected light and performs biological feature detection based on the reflected light. During this process, the incident light is absorbed and diffused under effects of the blood in the tissue and then the reflected light to be transmitted to the reflector is formed. Since the blood in the tissue may be periodically changed, the reflected light may be also changed, and the biological feature may be obtained by sensing and analyzing the reflected light. Analogously, with respect to the light transmission theory, the biological feature may be obtained by sensing and analyzing the transmitted light.

In the prior art, for example, if biological feature detection is implemented by combining the biological feature detection function with an earphone, the entire dimension of the earphone is great, and wearing comfort is poor.

SUMMARY

Embodiments of the present application are intended to provide an earplug apparatus and an electronic apparatus, to at least solve the above technical problem in the prior art.

Accordingly, embodiments of the present application provide an earplug apparatus. The earplug apparatus includes: a biological feature detection module, the biological feature detection module being arranged in the earplug apparatus and being configured to be fit in a region enclosed by an outer ear canal and an ear canal entrance; where the biological feature detection module includes a light emitting unit and a light receiving unit, where the light emitting unit is configured to emit light to the enclosed region, the light emitted by the light emitting unit is processed by an ear tissue in the enclosed region and transmitted to the light receiving unit, and the light receiving unit is configured to convert photoelectrically the received light to an original electrical signal for biological feature detection.

Optionally, in any embodiment of the present application, the earplug apparatus includes a sound conduction chamber; where the biological feature detection module is positioned on an outer wall of the sound conduction chamber.

Optionally, in any embodiment of the present application, a light transmission passage is arranged above the light emitting unit and/or the light receiving unit; where the light transmission passage is configured to enable the light emitted by the light emitting unit to be transmitted to the enclosed region and enable the light processed by the ear issue in the enclosed region to be transmitted to the light receiving unit; or a light guiding unit is arranged above the light emitting unit and/or the light receiving unit; where the light guiding unit is configured to guide the light emitted by the light emitting unit to enclosed region and guide the light processed by the ear tissue in the enclosed region to the light receiving unit.

Optionally, in any embodiment of the present application, the earplug apparatus includes: a sound conduction chamber; where the light transmission passage or the light guiding unit is arranged on an in-ear earmuff in a periphery of an outer wall of the sound conduction chamber.

Optionally, in any embodiment of the present application, the earplug apparatus further includes: a flexible member connecting the light emitting unit and the light receiving unit, to adjust a relative position and/or a relative angle between the light emitting unit and the light receiving unit.

Optionally, in any embodiment of the present application, an included angle formed between a normal of the light emitting unit facing an outer surface of the enclosed region and a normal of the light receiving unit facing the outer surface of the enclosed region is greater than or equal to 0 degree, but does not exceed 180 degrees.

Optionally, in any embodiment of the present application, a light shielding unit is arranged between the light emitting unit and the light receiving unit; where the light shielding unit is configured to prevent the light emitted by the light emitting light from being directly transmitted to the light receiving unit without being processed by the ear tissue in the enclosed region.

Optionally, in any embodiment of the present application, the earplug apparatus further includes a processing circuit and/or a control circuit. The processing circuit is at least configured to convert the original electrical signal to a digital signal and process the digital signal. The control circuit is at least configured to control the light emitting unit to emit light and control the light receiving unit to receive the light.

Optionally, in any embodiment of the present application, the earplug apparatus further includes a processor. The processor is configured to obtain a biological feature based on the original electrical signal.

Optionally, in any embodiment of the present application, the earplug apparatus further includes a protective cover. The protective cover is arranged above the light emitting unit and/or the light receiving unit.

Optionally, in any embodiment of the present application, the earplug apparatus further includes a light shielding layer arranged above the protective cover. The light shielding layer is configured to prevent the light emitted by the light emitting light from being directly transmitted to the light receiving unit without being processed by the ear tissue.

Optionally, in any embodiment of the present application, the region enclosed by the outer ear canal and the ear canal entrance of the ear includes: an outer auditory canal, or a tragus inner-side region, a concha cavity region, a supratragic notch region or an intertragic notch region that is connected to the outer auditory canal.

Optionally, in any embodiment of the present application, the light receiving unit is further configured to process the photoelectrically converted signal to generate an original electrical signal for determining a wearing state of the electronic apparatus.

Embodiments of the present application further provide an electronic apparatus. The electronic apparatus includes the earplug apparatus as described in any one of the above embodiments.

In embodiments of the present application, the biological feature detection module is arranged in the earplug apparatus and is configured to fit in a region enclosed by an outer ear canal and an ear canal entrance; and the biological feature detection module includes a light emitting unit and a light receiving unit, where the light emitting unit is configured to emit light to the enclosed region, the light emitted by the light emitting unit is processed by an ear tissue in the enclosed region and transmitted to the light receiving unit, and the light receiving unit is configured to convert the received light to an original electrical signal for biological feature detection. In this way, the entire dimension of the final product is small, and wearing comfort is enhanced.

DETAILED DESCRIPTION

Figure 1:
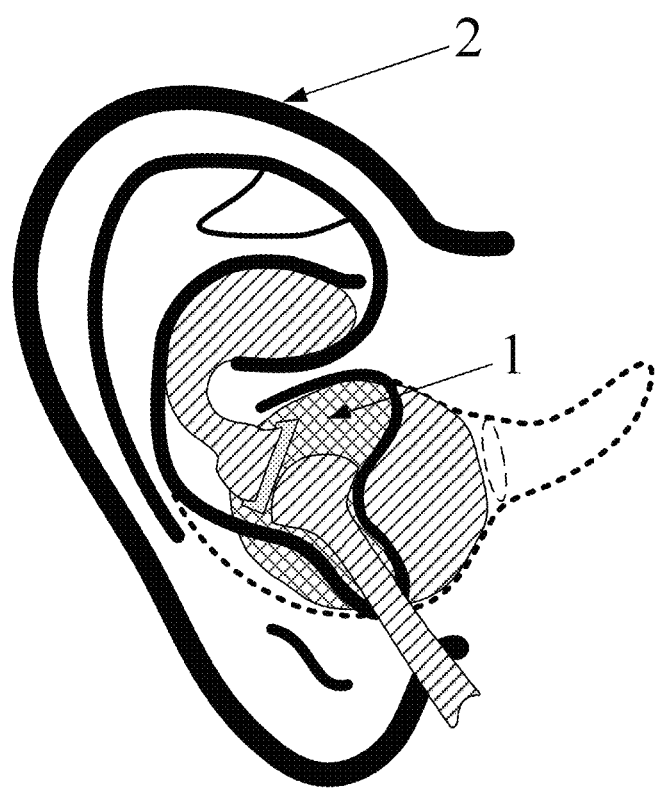
FIG. 1 is a schematic structural diagram of an earplug apparatus according to the first embodiment of the present application.

Practice of the present application is described in detail with reference to drawings and specific embodiments, such that the practice of addressing the technical problem using the technical means according to the present application and achieving the technical effects may be better understood and conducted.

According to an embodiment of the present application hereinafter, an earplug apparatus includes: a biological feature detection module, the biological feature detection module being arranged in the earplug apparatus and being configured to fit in a region enclosed by an outer ear canal and an ear canal entrance; where the biological feature detection module includes a light emitting unit and a light receiving unit, where the light emitting unit is configured to emit light to the enclosed region, the light emitted by the light emitting unit is processed by an ear tissue in the enclosed region and transmitted to the light receiving unit, and the light receiving unit is configured to convert the received light to an original electrical signal for biological feature detection.

In the embodiment of the present application, the earplug apparatus may be an earphone, a hearing aid or the like, which may be arranged at the ear, and have a full-in-ear structure, a semi-in-ear structure or an earplug structure.

In the embodiment of the present application, the earplug apparatus may be applied to biological feature detection for human beings, and may also be applied to biological feature detection for animals.

In the embodiment of the present application, the biological feature may be a heart rate feature, a blood oxygen feature or a blood pressure feature, or may be any biological feature that may be detected by other biological feature detection modules.

In the embodiments hereinafter of the present application, specifically, description is given by using the application of the above earplug apparatus to an earphone as an example, which is equivalent to the case where the earphone in one aspect implements a sound playing function and in another aspect implements a biological feature detection function. However, it should be noted that in other embodiments, the sound playing function may be omitted and only the biological feature detection function is implemented, for example, implementing the earplug apparatus in a hearing aiding manner.

The laws applicable to the biological feature detection according to the present application include, but not limited to, light reflection or light projection laws. In the embodiments hereinafter, description is given by using the case where the biological feature detection is implemented based on the light reflection law as an example.

The biological feature detection applicable to the light reflection law includes, but not limited to, biological feature detection based on a photoplethysmogram signal. In the embodiments hereinafter, description is given by using the case where the biological feature detection is implemented by using the photoplethysmogram signal based on the light reflection law as an example.

FIG. 1 is a schematic structural diagram of an earplug apparatus according to the first embodiment of the present application. As illustrated in FIG. 1, in this embodiment, an earplug apparatus 1 is practiced in the form of earphone, or it may be understood that the earplug apparatus is integrated with a conventional earphone structure. For clear description of application of the earplug apparatus, FIG. 1 also schematically illustrates an ear 2.

Figure 2:
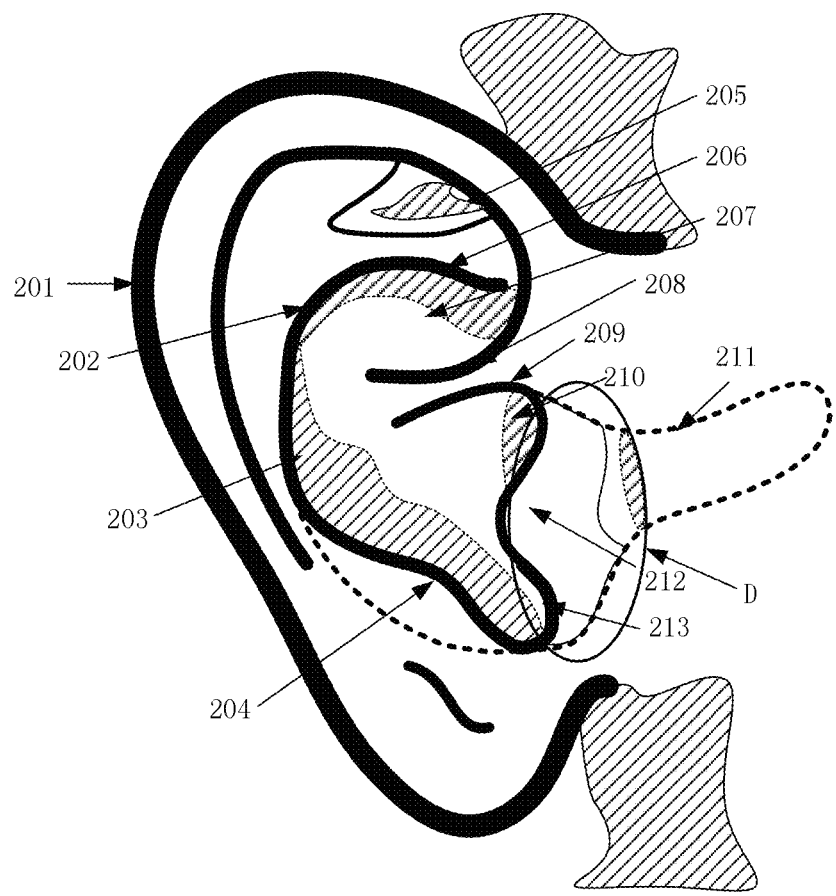
FIG. 2 is a schematic diagram of candidate regions of a detection surface of an ear according to the second embodiment of the present application.

FIG. 2 is a schematic diagram of candidate regions of a detection surface of an ear according to the second embodiment of the present application. As illustrated in FIG. 2, corresponding to FIG. 1, a portion of the features of the ear 2 include: a helix 201, an antihelix 202, an auricular concha 203, an antitragus 204, a triangular fossa 205, an inferior crus of antihelix 206, a cimba concha 207, a crus of helix 208, a supratragic notch 209, an ear canal entrance 210, an ear canal 211, a tragus 212, and an intertragic notch 213.

For close combination with the conventional structure of the earphone and reduction of the entire volume of the earphone as much as possible, in the embodiment of the present application, the biological feature detection module in the earplug apparatus is configured to fit in a region enclosed by an outer ear canal and an ear canal entrance, where the region enclosed by the outer ear canal and the ear canal entrance is used as a detection surface. Specifically, for example, the biological feature detection module fits in the outer ear canal (for example, attached to the outer ear canal), or the biological feature detection module fits in any of the following regions that are connected to the outer ear canal: an outer auditory canal, or a tragus inner-side region, a concha cavity region, a supratragic notch region or an intertragic notch region. Referring to FIG. 2, D represents the region enclosed by the outer ear canal and the ear canal entrance.

Figure 3:
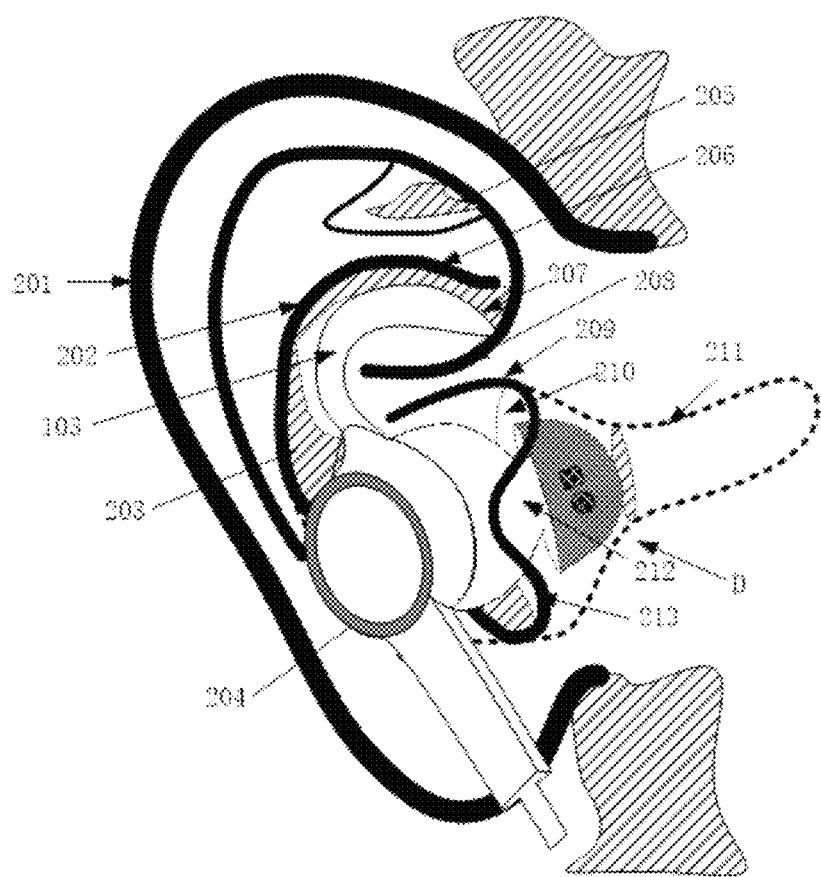
FIG. 3 is a schematic structural diagram of an earplug apparatus according to the third embodiment of the present application.

FIG. 3 is a schematic structural diagram of an earplug apparatus according to the third embodiment of the present application. As illustrated in FIG. 3, as described above, an in-ear earphone is used to implement the above earplug apparatus, that is, the earplug apparatus includes a sound conduction chamber, and the biological feature detection module is positioned on an outer wall of the sound conduction chamber (not illustrated in FIG. 3). Specifically, the light emitting unit 101 and the light receiving unit 102 in the biological feature detection module are arranged on an outer surface of the outer wall of the sound conduction chamber, such that the entire volume of the entire in-ear earphone is further reduced, and the earphone is comfortably worn.

In this embodiment, during specific implementation, the sound conduction chamber may be a cylinder or a prism, and correspondingly, the entire shape of the outer wall of the sound conduction chamber is a cylinder or a prism.

Further, in this embodiment, an in-ear earmuff is further arranged on a periphery of the outer wall of the sound conduction chamber, where the in-ear earmuff covers the outer wall of the sound conduction chamber. The in-ear earmuff may be made of a silica gel, a soft rubber or the like material. During wearing, the in-ear earplug may extrude an inner surface of the ear, such that the in-ear earphone is securely worn.

In this embodiment, by reference to the arrangement positions of the light emitting unit 101 and the light receiving unit 102 on the outer wall of the sound conduction chamber, a light transmission passage or a light guiding unit (not illustrated in FIG. 3) is arranged at the corresponding position of the in-ear earmuff, where the light transmission passage or the light guiding unit is configured to enable the light emitted by the light emitting unit 101 to be transmitted to the detection surface of the ear and enable the light processed by the ear to be transmitted to the light receiving unit 102. For the details, reference may be made to the disclosure of the drawings hereinafter.

Specifically, if the earplug apparatus includes a light transmission passage, the light transmission passage is arranged above the light emitting unit and/or the light receiving unit; and if the earplug apparatus includes a light guiding unit, the light guiding unit is arranged above the light emitting unit and/or the light receiving unit.

In this embodiment, the earplug apparatus further includes a wearing assisting mechanism 103, configured to enable the earplug apparatus to be securely worn on the ear, which further ensures that during the biological feature detection process, the relative position between the light emitting unit 101 and the light receiving unit 102 and the detection surface are relatively fixed. In this way, the detection accuracy of the biological feature detection is further improved. In a specific application scenario, the wearing assisting mechanism 103 is attached to the cimba concha 207. However, in other scenarios, the wearing assisting mechanism 103 may also be closely attached to the other feature regions of the ear according to the actual needs, as long as the earplug apparatus is securely worn on the ear.

In a specific application scenario, the wearing assisting mechanism 103 may be detachable from the earplug apparatus, such that the wearing assisting mechanism 103 is assembled to the earplug apparatus where the biological feature detection is desired. However, where the biological feature detection is not desired, the wearing assisting mechanism 103 is detached from the earplug apparatus, such that the earphone and the wearing assisting mechanism 103 are flexibly used. The wearing assisting mechanism 103 may be a structure member of the earplug apparatus, or may be not a structure member of the earplug apparatus but an assembly of the earplug apparatus.

Figure 4:
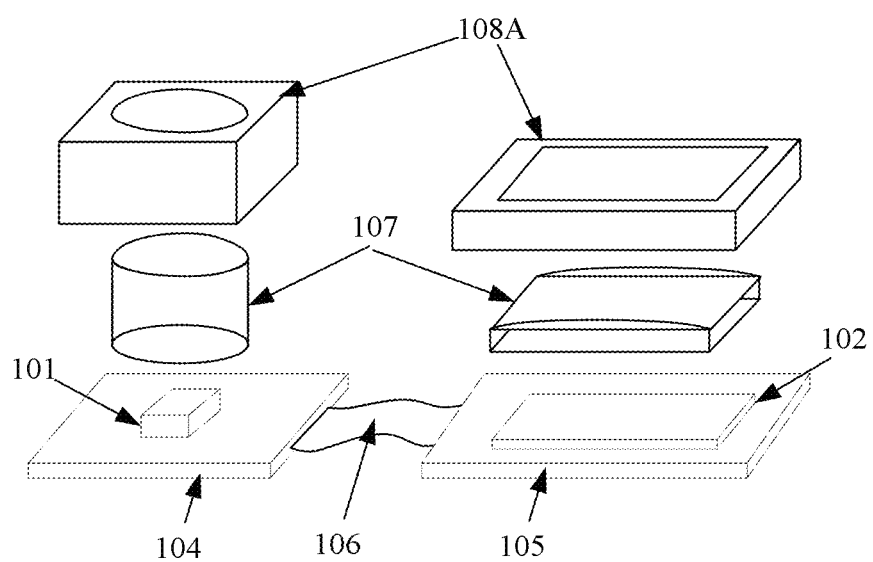
FIG. 4 is a schematic diagram of arrangement of a light emitting unit and a light receiving unit according to the fourth embodiment of the present application.

FIG. 4 is a schematic diagram of arrangement of a light emitting unit and a light receiving unit according to the fourth embodiment of the present application. As illustrated in FIG. 4, the earplug apparatus may further includes: a first substrate 104, a second substrate 105, a flexible member 106 and a light guiding unit 107; where the light emitting unit 101 is arranged on the first substrate 104, and the light receiving unit 102 is arranged on the second substrate 105. In this embodiment, the first substrate 104 and the second substrate 105 are both rigid substrates.

Referring to the above embodiments, if the biological feature detection module is positioned on the outer wall of the sound conduction chamber, specifically, the first substrate 104 and the second substrate 105 are arranged on the outer wall of the sound conduction chamber, such that the biological feature detection apparatus is positioned on the outer wall of the sound conduction chamber.

It should be noted that in other embodiments, alternatively, the light emitting unit 101 and the light receiving unit 102 may also be arranged on the same rigid substrate or flexible substrate, or respectively arranged on two flexible substrates; or either the first substrate or the second substrate is a flexible substrate, or both the first substrate and the second substrate are flexible substrates. Further, the flexible member may be a partial structure of the flexible substrate.

In this embodiment, the light emitting unit 101 is approximately a columnar light source, and the light receiving unit 102 is approximately a planar array to receive the light with a greater light sensing area as much as possible.

In this embodiment, the light emitting unit 101 and the light receiving unit 102 are connected to each other via the flexible member 106. The flexible member is configured to adjust a relative position and/or a relative angle between the light emitting unit 101 and the light receiving unit 102.

Optionally, in this embodiment, the relative position is a linear distance between a geometric center of the light emitting unit 101 and a geometric center of the light receiving unit 102, and/or the relative angle is an included angle formed between a normal of the light emitting unit 101 facing towards an outer surface of the enclosed region and a normal of the light receiving unit 102 facing towards the outer surface of the enclosed region.

Optionally, in a specific application scenario, an included angle formed between a normal of the light emitting unit 101 facing an outer surface of the enclosed region and a normal of the light receiving unit 102 facing the outer surface of the enclosed region is greater than or equal to 0 degree, but does not exceed 180 degrees. When the included angle is greater than 0 degree but does not exceed 180 degrees, in one aspect, the earplug apparatus may fit in the region enclosed by the outer ear canal and the ear canal entrance of the ear better and in another aspect, an action distance of the light emitted by the light emitting unit 101 in the ear tissue may be increased, which prevents excessive light from being reflected by the inner surface of the ear and then directly transmitted to the light receiving unit 102. In this way, the accuracy of the biological feature detection is further improved.

In this embodiment, the light guiding unit 107 is configured to guide the light emitted by the light emitting unit 101 to the detection surface, and/or guide the light processed by the ear tissue to the light receiving unit 102. Specifically, a light guiding unit 107 may be arranged on each of the light emitting unit 101 and the light receiving unit 102. That is, two light guiding units 107 are included. The two light guiding units 107 may be integrally arranged or separately arranged. That is, the light guiding unit 107 on the light emitting unit 101 and the light guiding unit 107 on the light receiving unit 102 may be integrally arranged or separately arranged. However, it should be noted that a light guiding unit 107 may also be arranged on either the light emitting unit 101 or the light receiving unit 102. That is, one light guiding unit 107 is included. In this embodiment, the light guiding unit 107 improves efficiency of light transmission and lowers entire power consumption of the apparatus.

In another embodiment, alternatively, a light transmission passage may also be arranged by reference to the arrangement of the light guiding unit 107.

In a specific application scenario, the light guiding unit 107 may slightly protrude from the shell of the earphone to be tightly attached to the detection surface of the ear. In this way, efficiency of light transmission is improved, the signal-to-noise ratio is enhanced, and the entire power consumption of the earplug apparatus is lowered.

In this embodiment, a surface, towards the detection surface, of the light guiding unit 107 is defined to mate with the detection surface of the ear. If the detection surface is a flat surface, the surface, facing towards the detection surface, of the light guiding unit 107 is a flat surface; if the detection surface is an arc surface, the surface, facing towards the detection surface, of the light guiding unit 107 is an arc surface; and if the detection surface is an irregular curve surface, the surface, facing towards the detection surface, of the light guiding unit 107 is also an irregular curve surface. It should be noted that the surface, facing towards the detection surface, of the light guiding unit 107 may be only defined to mate with the detection surface according to the actual needs of the structural design. For example, if the light guiding unit 107 is made of an elastic material, the light guiding unit 107 may mate with the detection surface in any shape.

In this embodiment, the surface, facing towards the detection surface, of the light guiding unit 107 is arc-shaped, and as much as possible seamlessly attached to the tragus inner-side region, such that the efficiency of light transmission is improved. In addition, due to existence of the flexible member 106, the attachment position of the light guiding unit 107 and the detection surface may be flexibly adjusted.

In the embodiment as illustrated in FIG. 4, the earplug apparatus further includes a first light shielding unit 108A; where the first light shielding unit 108A is positioned above the light emitting unit 101 and the light receiving unit 102 respectively to prevent the light emitted by the light emitting unit 101 from being directly transmitted to the light receiving unit 102 without being processed by the ear tissue, and to hence improve the accuracy of the biological feature detection. The first light shielding unit 108A may be specifically arranged above the light guiding unit 107. In addition, a through hole that allows the light to pass through is arranged on the first light shielding unit 108A, to ensure that the light emitted by the light emitting unit 101 and the light processed by the ear tissue are transmitted to the light receiving unit 102.

Figure 5:
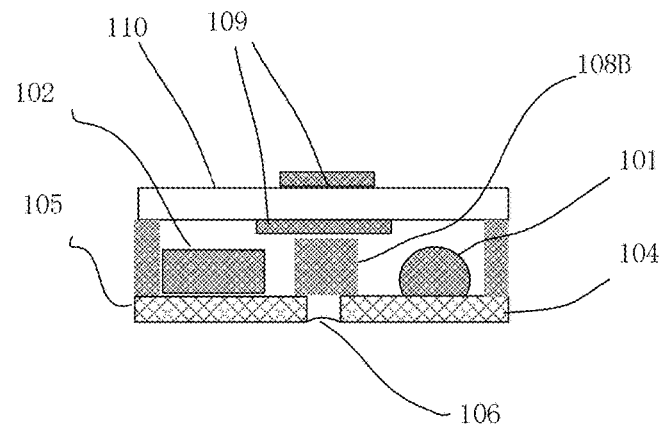
FIG. 5 is a schematic diagram of arrangement of a light emitting unit and a light receiving unit according to the fifth embodiment of the present application.

FIG. 5 is a schematic diagram of arrangement of a light emitting unit and a light receiving unit according to the fifth embodiment of the present application. As illustrated in FIG. 5, the earplug apparatus may further include: a second light shielding unit 108B, a light shielding layer 109 and a protective cover 110 configured to protect at least one of the light emitting unit 101 and the light receiving unit 102.

When the earplug apparatus includes the above light guiding member, the light guiding member may be simultaneously used as the protective cover 110 or the protective cover 110 may be simultaneously used as the light guiding member. In this way, the volume of the in-ear earphone is further reduced, such that the entire structure of the in-ear earphone is relatively compact.

In this embodiment, the second light shielding unit 108B is configured to prevent the light emitted by the light emitting unit from being directly transmitted to the light receiving unit without being processed by the ear tissue. Specifically, for example, the light emitted by the light emitting unit 101 is shielded or absorbed, to prevent the light emitted by the light emitting unit 101 from being directly transmitted to the light receiving unit 102 without being processed by the ear tissue and to hence improve the accuracy of the biological feature detection.

In this embodiment, the second light shielding unit 108B is specifically arranged between the light emitting unit 101 and the light receiving unit 102.

In a specific application scenario, the second light shielding unit 108B and the outer wall of sound conduction chamber are defined as an integral structure; or the second light shielding unit 108B, the light emitting unit 101 and the light receiving unit 102 are defined as an integral structure.

During specific implementation, when the protective cover 110 is meanwhile reused as the light guiding unit, the protective cover may slightly protrude from the shell of the earphone to be tightly attached to the detection surface of the ear. In this way, efficiency of light transmission is improved, the signal-to-noise ratio is enhanced, and the entire power consumption of the earplug apparatus is lowered.

The light shielding layer 109 is arranged above the protective cover 110. Specifically, for example, the light shielding layer 109 is arranged on an upper surface or a lower surface of the protective cover 110, or on both an upper surface and a lower surface of the protective cover 110. The light shielding layer 109 is configured to prevent the light emitted by the light emitting unit 101 from being directly transmitted to the light receiving unit 102 without being processed by the ear tissue, such that the accuracy of the heart rate detection is improved. The area of the light shielding layer 109 may be flexibly defined according to the actual needs, and the position of the light shielding layer 109 on the protective cover 110 may be flexible defined according to the actual needs as long as the accuracy of the heart rate detection is improved.

In a specific application scenario, the light shielding layer is at least one of an ink layer, an adhesive layer and a light absorption film layer.

Figure 6:
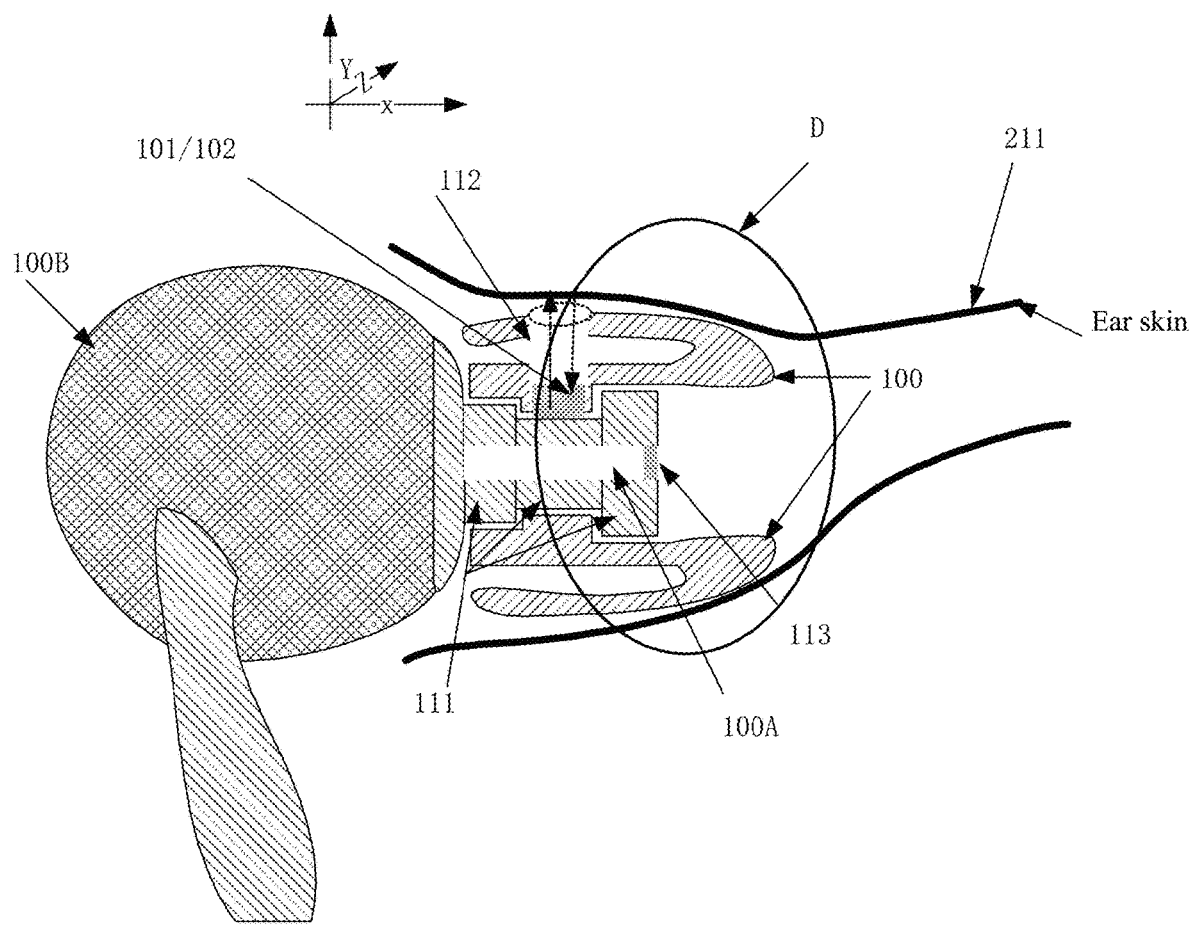
FIG. 6 is one schematic structural diagram of an earplug apparatus according to the sixth embodiment of the present application.
Figure 7:
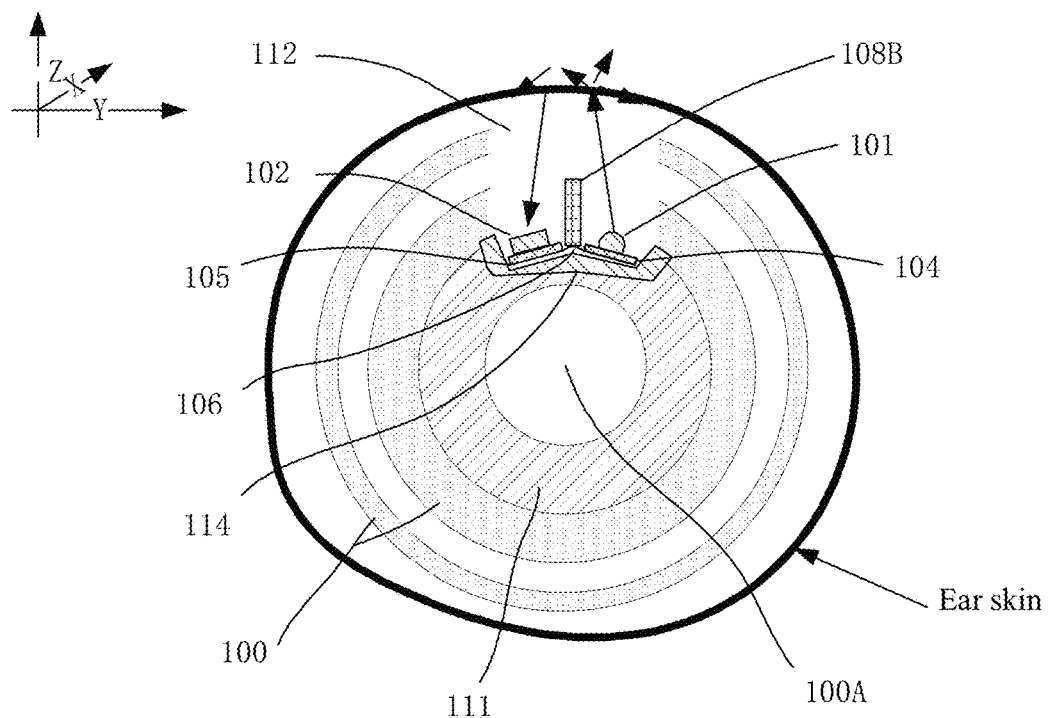
FIG. 7 is another schematic structural diagram of the earplug apparatus according to the sixth embodiment of the present application.
Figure 8:
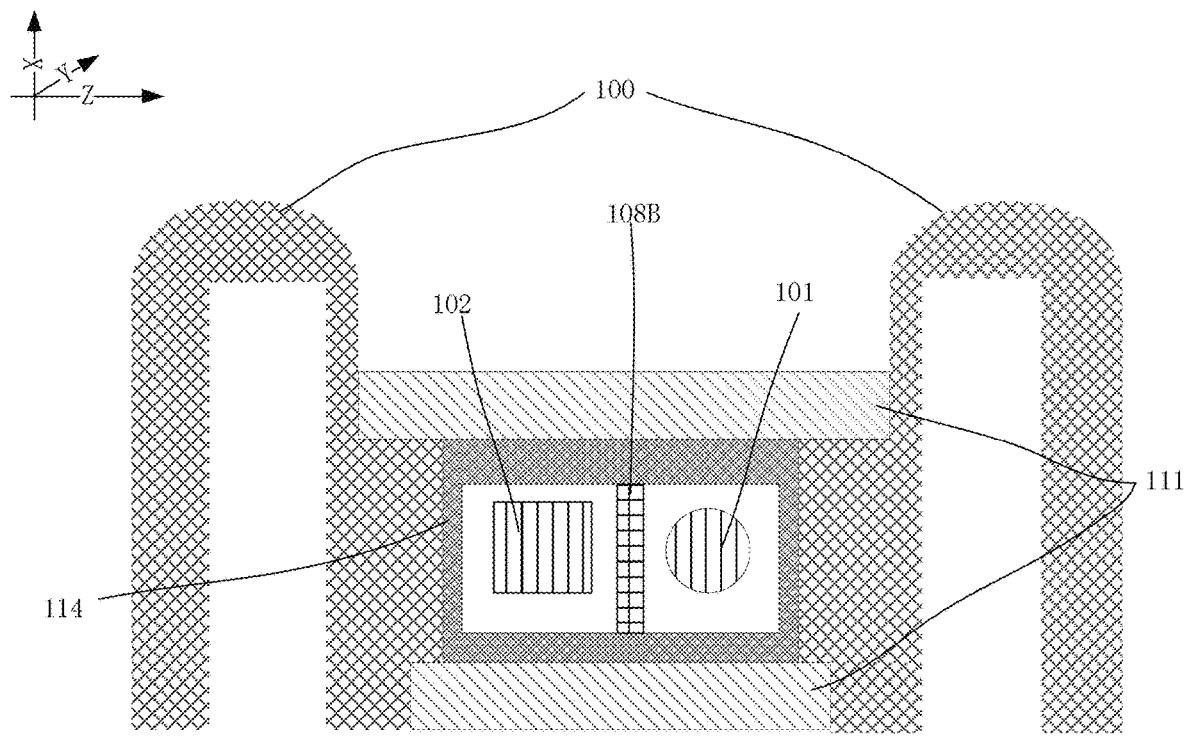
FIG. 8 is still another schematic structural diagram of the earplug apparatus according to the sixth embodiment of the present application.

FIG. 6 is one schematic structural diagram of an earplug apparatus according to the sixth embodiment of the present application. FIG. 7 is another schematic structural diagram of the earplug apparatus according to the sixth embodiment of the present application. FIG. 8 is still another schematic structural diagram of the earplug apparatus according to the sixth embodiment of the present application. As illustrated in FIG. 6, FIG. 7 and FIG. 8, by reference to the arrangement positions of the light emitting unit 102 and the light receiving unit 102 on an outer wall 111 of a sound conduction chamber 100A, a light transmission passage 112 (or a light guiding unit) is arranged at the corresponding position of an in-ear earmuff 100, where the light transmission passage 112 (or the light guiding unit) is configured to enable the light emitted by the light emitting unit 101 to be transmitted to the detection surface of the ear and enable the light processed by the ear to be transmitted to the light receiving unit 102. In addition, the in-ear earphone further includes an earphone body 100B, configured to process data and the like relevant to sound playing.

In this embodiment, by reference to the arrangement positions of the light emitting unit 101 and the light receiving unit 102 on the outer wall 111 of the sound conduction chamber, a through hole is defined at the corresponding position of the in-ear earmuff 100; where the through hole is used as the light transmission passage 112 (or a light guiding tube is arranged in the through hole, and the light guiding is used as the light guiding unit).

In this embodiment, the in-ear earphone is further provided with a dust-proof mesh 113.

When a light guiding tube is arranged in the through hole, the light guiding tube and the in-ear earmuff are defined as an integral structure via a double-color injection; or the light guiding tube is arranged on the in-ear earmuff to define a split structure.

In addition, in this embodiment, the in-ear earmuff 100 may be supported by an elastic material such as a silica gel, a soft rubber or the like. During wearing, through pressing, the earmuff is in close contact with the skin on the inner surface of the ear, such that the light emitting unit 101 and the light receiving unit 102 are prevented from sliding relative to the detection surface during the movement process. In this way, the accuracy of the biological feature detection is further improved.

In addition, in a specific application scenario, the light emitting unit 101 and the light receiving unit 102 may be arranged on the outer wall 111 of the sound conduction chamber via a fixing structure 114. Specifically, the outer wall 111 of the sound conduction chamber is subjected to surface cutting at the position of the biological feature detection module, such that a flatness is ensured, and then the fixing structure is arranged on the cut surface.

Based on any embodiment of the present application, the earplug apparatus may further include a processing circuit and/or a control circuit. The processing circuit is at least configured to convert the original electrical signal to form a digital signal and filter the digital signal. The control circuit is at least configured to control the light emitting unit to emit light and control the light receiving unit to receive the light.

It should be noted that functionality of the processing circuit may be extended according to the actual needs, which is not limited to analog-to-digital conversion and filter processing.

Optionally, based on any embodiment of the present application, the earplug apparatus may further include: a processor; where the processor is at least configured to obtain a biological feature according to the original electrical signal. During biological feature detection performed by the processor based on the original electrical signal, a biological feature signal may be specifically extracted from a digital signal experiencing analog-to-digital conversion and filter processing by the processing circuit; or the processor directly performs analog-to-digital conversion and filtering for the original electrical signal, and then performs biological feature detection. It should be noted that the processor may be an independently configured microprocessor, or may be the processor of the terminal connected to the earphone.

During specific implementation, the light emitting unit 101 and the light receiving unit 102 may be separately arranged from the processing circuit in terms of physical aspect, or may be integrally arranged with the processing circuit.

In specific implementation, the light emitting unit 101, the light receiving unit 102, the processing circuit and the processor are physically separated structures, or may be integrated to form a chip structure.

In specific implementation, the earplug apparatus according to the above embodiment may include a plurality of light emitting units and one light receiving unit, to improve emission efficiency of incident light.

In specific implementation, the earplug apparatus according to the above embodiment may include a plurality of light receiving units and one light emitting unit, to improve receiving efficiency of light.

In the above embodiment including the flexible member, due to presence of the flexible member, the relative position and the relative angle between the light emitting unit and the light receiving unit may be randomly adjusted, such that the earplug apparatus is suitable for the detection surface having any shape.

In the above embodiment, even during the movement process, since the light emitting unit 101 and/or the light receiving unit 102 is arranged on the outer wall of the sound conduction chamber or on the in-ear earplug, sliding of the earplug apparatus relative to the detection surface may be prevented, such that the stability and strength of the detection signal are improved, and meanwhile adverse impacts caused by the movement to the signal-to-noise ratio of the detection signal may be weakened or eliminated.

It should be noted that alternatively, in other embodiments, the support unit is an in-ear earmuff.

In addition, it should be noted that in the above embodiments, the earplug apparatus may simultaneously include a plurality of structure members. However, persons of ordinary skill in the art may omit some of the structure members according to the actual needs.

Further, in the above embodiments, during specific practice of the product, the light emitting unit, the light receiving unit, the processing circuit, the processor and the like may form the biological feature detection module.

With reference to the above biological feature detection based on the light reflection law, the biological feature detection may be also be performed based on the light projection law. Further, the arrangements of the light emitting unit and the light receiving unit, and the relationships of the light emitting unit and the light receiving unit and the other structure members may be adaptively improved or adjusted according to the actual needs without departing from the principle of the present application.

An embodiment of the present application further provides an electronic apparatus which includes the earplug apparatus according to the embodiments of the present application. The electronic apparatus includes the earplug apparatus according to the above embodiment, and the electronic apparatus may be a full-in-ear earphone or may be a semi-in-ear earphone or a hearing aid or the like. Optionally, the electronic apparatus may be a human placental ear wearing apparatus having only the biological feature detection function.

In addition, in other embodiments, the light receiving unit may be further configured to convert the received light to an original electrical signal for determining a wearing state of the electronic apparatus.

Specifically, whether the electronic apparatus is worn is directly determined based on the strength of the original electrical signal; or whether a biological feature is detected is firstly determined according to the original electrical signal, and then whether the electronic apparatus is worn is further determined.

The above described apparatus embodiments are merely for illustration purpose only. The modules which are described as separate components may be physically separated or may be not physically separated, and the components which are illustrated as modules may be or may not be physical modules, that is, the components may be located in the same position or may be distributed into a plurality of network modules. A part or all of the modules may be selected according to the actual needs to achieve the objectives of the technical solutions of the embodiments. Persons of ordinary skill in the art may understand and implement the present invention without paying any creative effort.

Although the preferred embodiments of the present application are described above, once knowing the basic creative concept, a person skilled in the art can make other modifications and variations to these embodiments. Therefore, the appended claims are intended to be construed as covering the preferred embodiments and all the modifications and variations falling within the scope of the present application. Obviously, a person skilled in the art can make various modifications and variations to the present application without departing from the spirit and scope of the present application. In this way, the present application is intended to cover the modifications and variations if they fall within the scope of the appended claims of the present application and equivalent technologies thereof.

What is claimed is:

1. An earplug apparatus, comprising:
an earphone body;
a sound conduction chamber that is formed by an outer wall coupled with the earphone body;
a biological feature detection module, the biological feature detection module being arranged in the earplug apparatus and being configured to be fit in a region enclosed by an outer ear canal and an ear canal entrance; wherein the biological feature detection module comprises a light emitting unit and a light receiving unit, the light emitting unit is configured to emit light to the enclosed region, the light emitted by the light emitting unit is processed by an ear tissue in the enclosed region and transmitted to the light receiving unit, and the light receiving unit is configured to convert the received light photo electrically to an original electrical signal for biological feature detection,
wherein the biological feature detection module is disposed in a concave that is formed on a surface of the outer wall of the sound conduction chamber.

2. The earplug apparatus according to claim 1, further comprising a flexible member connecting the light emitting unit and the light receiving unit, to adjust at least one of a relative position and a relative angle between the light emitting unit and the light receiving unit.

3. The earplug apparatus according to claim 1, wherein:
a light transmission passage is provided above at least one of the light emitting unit and the light receiving unit; wherein the light transmission passage is configured to enable the light emitted by the light emitting unit to be transmitted to the enclosed region and enable the light processed by the ear tissue in the enclosed region to be transmitted to the light receiving unit; or
a light guiding unit is provided above at least one of the light emitting unit and the light receiving unit; wherein the light guiding unit is configured to guide the light emitted by the light emitting unit to the enclosed region and guide the light processed by the ear tissue in the enclosed region to the light receiving unit.

4. The earplug apparatus according to claim 3, wherein the light transmission passage or the light guiding unit is arranged on an in-ear earmuff in a periphery of the outer wall of the sound conduction chamber.

5. The earplug apparatus according to claim 4, further comprising a flexible member connecting the light emitting unit and the light receiving unit, to adjust at least one of a relative position and a relative angle between the light emitting unit and the light receiving unit.

6. The earplug apparatus according to claim 3, further comprising a flexible member connecting the light emitting unit and the light receiving unit, to adjust at least one of a relative position and a relative angle between the light emitting unit and the light receiving unit.

7. The earplug apparatus according to claim 1, further comprising a flexible member connecting the light emitting unit and the light receiving unit, to adjust at least one of a relative position and a relative angle between the light emitting unit and the light receiving unit.

8. The earplug apparatus according to claim 1, wherein an included angle formed between a normal of the light emitting unit facing an outer surface of the enclosed region and a normal of the light receiving unit facing the outer surface of the enclosed region is greater than or equal to 0 degree, and does not exceed 180 degrees.

9. The earplug apparatus according to claim 1, wherein a light shielding unit is provided between the light emitting unit and the light receiving unit; wherein the light shielding unit is configured to prevent the light emitted by the light emitting unit from being directly transmitted to the light receiving unit without being processed by the ear tissue in the enclosed region.

10. The earplug apparatus according to claim 1, further comprising at least one of:
a processing circuit; wherein the processing circuit is at least configured to convert the original electrical signal to a digital signal and process the digital signal; and
a control circuit, wherein the control circuit is at least configured to control the light emitting unit to emit light and control the light receiving unit to receive the light.

11. The earplug apparatus according to claim 1, further comprising: a processor;
wherein the processor is configured to obtain a biological feature based on the original electrical signal.

12. The earplug apparatus according to claim 1, further comprising: a protective cover; wherein the protective cover is arranged above the light emitting unit and the light receiving unit.

13. The earplug apparatus according to claim 12, further comprising a light shielding layer arranged above the protective cover; wherein the light shielding layer is configured to prevent the light emitted by the light emitting unit from being directly transmitted to the light receiving unit without being processed by the ear tissue.

14. The earplug apparatus according to claim 1, wherein the region enclosed by the outer ear canal and the ear canal entrance of the ear comprises: an outer auditory canal, or a tragus inner-side region, a concha cavity region, a supratragic notch region or an intertragic notch region that is connected to the outer auditory canal.

15. An electronic apparatus comprising an earplug apparatus, wherein the earplug apparatus comprises:
   an earphone body;
   a sound conduction chamber that is formed by an outer wall coupled with the earphone body; and
   a biological feature detection module, the biological feature detection module being arranged in the earplug apparatus and being configured to fit in a region enclosed by an outer ear canal and an ear canal entrance; wherein the biological feature detection module comprises a light emitting unit and a light receiving unit, the light emitting unit is configured to emit light to the enclosed region, the light emitted by the light emitting unit is processed by an ear tissue in the enclosed region and transmitted to the light receiving unit, and the light receiving unit is configured to convert the received light photo electrically to an original electrical signal for biological feature detection,
   wherein the biological feature detection module is disposed in a concave that is formed on a surface of the outer wall of the sound conduction chamber.

* * * * *